(12) United States Patent
Larsen

(10) Patent No.: US 8,008,002 B2
(45) Date of Patent: Aug. 30, 2011

(54) NUCLEIC ACID SEQUENCING

(75) Inventor: Frank Larsen, Oslo (NO)

(73) Assignee: QIAGEN GmbH, Hilden (DE)

( * ) Notice: Subject to any disclaimer, the term of this patent is extended or adjusted under 35 U.S.C. 154(b) by 542 days.

(21) Appl. No.: 10/599,351

(22) PCT Filed: Mar. 24, 2005

(86) PCT No.: PCT/IB2005/000763
§ 371 (c)(1),
(2), (4) Date: Aug. 22, 2008

(87) PCT Pub. No.: WO2005/093100
PCT Pub. Date: Oct. 6, 2005

(65) Prior Publication Data
US 2008/0311562 A1 Dec. 18, 2008

(30) Foreign Application Priority Data
Mar. 26, 2004 (GB) .................................. 0406864.9

(51) Int. Cl.
*C12Q 1/68* (2006.01)
*C12Q 1/66* (2006.01)
*C07H 21/04* (2006.01)

(52) U.S. Cl. ................................ 435/6; 435/8; 536/24.3

(58) Field of Classification Search ........................ None
See application file for complete search history.

(56) References Cited

U.S. PATENT DOCUMENTS
2001/0031467 A1 * 10/2001 Dapprich et al. ................. 435/6

FOREIGN PATENT DOCUMENTS

| WO | WO 92/15711 | 9/1992 |
|---|---|---|
| WO | WO 93/23562 | 11/1993 |
| WO | WO 94/01447 | 1/1994 |
| WO | WO 95/15974 | 6/1995 |
| WO | WO 97/23650 | 7/1997 |
| WO | WO 97/46711 | 12/1997 |
| WO | WO 98/13523 | 4/1998 |
| WO | WO 98/28440 | 7/1998 |
| WO | WO 00/20628 | 4/2000 |
| WO | WO 00/66604 | 11/2000 |
| WO | WO 01/90419 | 11/2001 |
| WO | WO 0190419 A2 * | 11/2001 |
| WO | WO 02/20837 | 3/2002 |
| WO | WO 03/095664 | 11/2003 |
| WO | WO 2004/001015 | 12/2003 |

OTHER PUBLICATIONS

Ronaghi et al., "A Sequencing Method based on Real-Time Pyrophosphate", in: Science, vol. 281, Jul. 17, 1998.
Kaneoka et al., "Solid-Phase Direct DNA Sequencing of Allele-Specific Polymerase Chain Reaction—Amplified HLA-DR Genes", in: Biotechniques, vol. 10, No. 1, 1991.
Finckh et al., Allele-specific PCR for simultaneous amplification of both alleles of a deletion polymorphism in intron 6 of the human dopamine 2 receptor gene (DRD2), in: DNA Sequence—The Journal of Sequencing and Mapping, vol. 6, pp. 87-94, 1996.
Sanger et al., "DNA Sequencing with chain-terminating inhibitors", in: Proc. Natl. Acad. Sci., vol. 74, No. 12, pp. 5463-5467, Dec. 1977.
Alderborn et al., "Determination of Single-Nucleotide Polymorphisms by Real-time Pyrophosphate DNA Sequencing", in: Genome Research, vol. 10, 2000, pp. 1249-1258.

* cited by examiner

*Primary Examiner* — Samuel C Woolwine
(74) *Attorney, Agent, or Firm* — Henry M. Feiereisen; Ursula B. Day

(57) ABSTRACT

A method is disclosed for determining a target nucleic acid sequence, where the target nucleic acid sequence is comprised in a preparation comprising a non-target nucleic acid sequence, the target nucleic acid sequence and the non-target nucleic acid sequence each having a first region of common sequence upstream of a first region of dissimilar sequence upstream of a second region of dissimilar sequence, and includes the steps of contacting the preparation with an oligonucleotide primer complementary to at least a portion of the first region of common sequence, under conditions to hybridise the primer thereto; contacting the preparation with a first labelled nucleotide bearing a first label, wherein the first labelled nucleotide is complementary to a first template nucleotide comprised in the first region of dissimilar sequence of either the target nucleic acid sequence or the non-target nucleic acid sequence, under conditions to incorporate the first labelled nucleotide either into the primer hybridised to the target nucleic acid sequence or into the primer hybridised to the non-target nucleic acid sequence but not into both; and subjecting the preparation to a sequencing reaction, thereby extending the primer to form one or more first-labelled sequencing products comprising the first labelled nucleotide and one or more non-first-labelled sequencing products comprising no first labelled nucleotide; and determining at least a portion of the sequence of the first-labelled sequencing products and/or the non-first-labelled sequencing products, thereby determining at least the second region of dissimilar sequence of the target nucleic acid sequence.

22 Claims, 6 Drawing Sheets

Step 1: Hybridisation of primer to template

Step 3: Removal of unused label

Step 4 : Standard sequencing reaction

Step 2: Allele-specific labeling B

NUCLEIC ACID SEQUENCING

BACKGROUND OF THE INVENTION

The present invention relates to a method of sequencing a nucleic acid. In particular, the invention relates to a method for determining a target nucleic acid sequence where the target nucleic acid sequence is comprised in a preparation comprising a non-target nucleic acid sequence. The invention also relates to a method for determining the haplotype of a subject.

The sequencing of nucleic acids, in particular DNA, is of fundamental importance in many areas of biological research, clinical diagnosis and treatment. Sequencing of DNA is typically carried out by a method based on the Sanger dideoxy chain-termination method (Sanger, F., Nicklen, S., and Coulson, A. R. (1977) "DNA Sequencing with chain-terminating inhibitors" PNAS USA 74:5463-5467). In this method, a labelled oligonucleotide primer complementary to a known sequence adjacent to the target sequence is used to initiate DNA polymerase-catalysed elongation into the target sequence. Typically, four polymerase reactions are carried out for each round of sequencing. Each reaction contains all four deoxynucleotides (dNTPs-dCTP, dTTP, dGTP and dATP) plus a small amount of one dideoxynucleotide (ddNTP-ddCTP, ddTTP, ddGTP or ddATP). Because ddNTPs have no 3' hydroxyl group, elongation of the nascent strand is occasionally terminated by incorporation of a ddNTP. Thus the sequencing reaction produces a series of labelled strands whose lengths are indicative of the location of a particular base in the sequence. The resultant labelled strands are typically separated according to size by polyacrylamide gel electrophoresis and visualised by detecting the label, for example by autoradiography where the primer was radiolabelled. More recently, the Sanger sequencing method has been adapted in various ways, in particular for large-scale automated sequencing using multiple fluorescent labels and capillary gel electrophoresis.

One problem with sequencing methods based on the Sanger method occurs when the target nucleic acid to be sequenced is provided in a preparation comprising one or more different nucleic acids or sequences which show some sequence identity to the target sequence. In particular, if a primer-binding sequence is found in both the target sequence and a second or further sequences, the sequencing reaction will lead to products which are derived from primer binding to the second or further sequences, as well as the target sequence. Where the target sequence diverges from the second or further sequences, the resultant gel or chromatograph will reveal two or more bases as being present at a particular location. Because the method does not allow discrimination between the products of the target sequence and the second or further sequences, the target sequence cannot be determined unambiguously.

This problem is particularly significant when it is desired to determine the sequence of one allele of a heterozygote pair at a polymorphic location in a single individual. Many eukaryotic cells are diploid, having two copies of most chromosomes, and sequence differences usually exist between each copy of a particular chromosome. Because DNA prepared from one individual will normally contain copies of both chromosomes, standard sequencing methods are unable to differentiate between sequences derived from each copy. Where there is a single nucleotide difference between each allele, the DNA sequence of each chromosome will nevertheless be clear (although it would not be possible to ascribe each sequence to a particular paternal or maternal chromosome). Where the polymorphism extends for two or more nucleotides, or where there are two or more polymorphic sites (alleles) separated by regions of common sequence, it is not possible to discern the sequence of the two alleles. In particular, standard sequencing methods are not able to determine the combination of alleles existing on a particular chromosome (the haplotype).

In the wave of interest spawned by the mapping of the human genome, interest has grown in the use of single nucleotide polymorphisms (SNPs) to identify target genes associated with disease or drug response. In some instances, the presence of a particular SNP alone may be sufficient to cause a particular disease or to explain the individual variability in sensitivity to drugs.

However, it is not clear how often knowledge of an individual SNP will have utility in the clinic or in drug development. Research has shown that in asthma, at least, the association of individual SNPs to form a complete haplotype may be more relevant in predicting drug response than knowledge of isolated individual SNPs. In many cases it may be necessary to obtain a haplotype sequence involving the characterisation of two or more SNPs on each chromosome. It is therefore highly desirable to determine the combination of SNPs that co-exist on a single chromosome.

HLA (human leukocyte antigen or human leukocyte associated antigen A) genotyping is one area where haplotyping is important. Determination of the two haplotype sequences of the HLA genes is crucial to the success of organ transplantation. The individual haplotypes of the donor must be matched with the recipient before transplantation to avoid rejection of the transplant. Methods for evaluating HLA allele types have been described in the past. One such method relies on performing family studies, which is very time-consuming. An alternative method based on DNA sequencing is disclosed in WO 97/23650. However, where heterozygous alleles exist, this method relies on prior knowledge of existing haplotype sequences, so that ambiguous bases can be ascribed to one allele or another.

Many of the methods used for haplotyping used in the past rely on preparing a composition comprising only a single haplotype sequence before sequencing. One way of doing this is by converting a diploid cell into a haploid cell. This requires a high investment, is labour intensive and slow but gives complete haplotype separation. Alternatively, human chromosomes can be cloned into yeast in order to get a haploid for that particular chromosome. This suffers from the same drawbacks in terms of time and cost.

One way of obtaining a preparation comprising only a single haplotype sequence is to amplify DNA by PCR using allele-specific primers. This type of approach for sequencing both alleles of a deletion polymorphism in intron 6 of the human dopamine 2 receptor gene (DRD2) is described in DNA Sequence Vol 6 (2), pp 87-94 (1996), Finck et al. In this method, allele-specific primers are used to amplify individual allele sequences by polymerase chain reaction (PCR). The primers are designed so that they produce amplicons of differing lengths, so that the products of each allele can be discriminated by agarose gel electrophoresis when both alleles are simultaneously amplified in the same reaction tube. The amplicons from each allele are then extracted from the gel and sequenced using conserved primers. The disadvantage of this approach is that it requires the prior knowledge of at least two, sufficiently separated regions of dissimilarity between the alleles so that appropriate allele-specific primers producing different-sized products can be designed. In addition, it requires a time-consuming gel separation and extraction step prior to sequencing.

A related approach is described in *Biotechniques* Vol 10 (1), pp 30, 32 and 34 (1991), Kaneoka et al. Biotinylated allele-specific oligonucleotide primers coupled to streptavidin-coated magnetic beads are used to amplify DNA from one haplotype by PCR, and then conserved primer is used for solid-phase direct DNA sequencing.

WO 92/15711 discloses a method for determining a major histocompatibility complex genotype of a subject in a sample containing nucleic acid. The method involves PCR amplification of the gene locus of interest, with all alleles for the gene locus to be sequenced being amplified with one conserved oligonucleotide primer pair and at least one allele for the gene locus being amplified with one conserved oligonucleotide primer and one non-conserved oligonucleotide primer. The amplicons for each allele are then sequenced with a conserved primer.

A different method for determining haplotype sequences involves analysis of PCR amplified sequences covering a polymorphic region by hybridisation rather than sequencing. PCR amplicons are contacted with oligonucleotide probes complementary to the sequence of either the maternal or paternal chromosome in a region comprising an SNP. Probes complementary to the maternal or paternal chromosomes are immobilised in different areas of a solid phase. A second set of oligonucleotide probes, labelled in a different way and complementary to the sequence of either the maternal or paternal chromosome in a region comprising a second SNP, is then used to identify which sequence at the first SNP is on the same chromosome as a particular sequence at the second SNP.

Other approaches have been adopted in the past for determining a target nucleic acid sequence when the target sequence is contained in a preparation comprising a non-target nucleic acid sequence. In one method described in WO 97/46711, a primer is selected that complements one strand but not the other, and an artificial mismatch is introduced into the primer. By selecting suitable hybridisation conditions so that stable duplexes form between the primer and one allele but not between the primer and the other allele, chain-extension sequencing of a single allele is achieved. A disadvantage of this method is that the selection of appropriate hybridisation conditions is time-consuming and not necessarily straightforward.

WO 00/20628 describes a method by which multiple genomic loci can be sequenced in the same reaction mixture. This method allows the sequencing of a second locus in the mixture by using primers which are longer than the longest product formed from the sequencing reaction in relation to a first locus. Different primers are used for each locus. However, this document does not disclose a method for haplotyping for particular alleles of a single locus.

SUMMARY OF THE INVENTION

Accordingly, the present invention aims to overcome the disadvantages of the prior art. In particular, the present invention aims to provide an improved method of determining a target nucleic acid sequence, where the target nucleic acid is comprised in a preparation comprising a non-target nucleic acid which has regions of common and dissimilar sequence to the target nucleic acid. The present invention also aims to provide an improved method for determining the haplotype of a subject.

Accordingly, the present invention provides a method for determining a target nucleic acid sequence, wherein the target nucleic acid sequence is comprised in a preparation comprising a non-target nucleic acid sequence, the target nucleic acid sequence and the non-target nucleic acid sequence each having a first region of common sequence upstream of a first region of dissimilar sequence upstream of a second region of dissimilar sequence, the method comprising:

(a) contacting the preparation with an oligonucleotide primer complementary to at least a portion of the first region of common sequence, under conditions to hybridise the primer thereto;

(b) contacting the preparation with a first labelled nucleotide bearing a first label, wherein the first labelled nucleotide is complementary to a first template nucleotide comprised in the first region of dissimilar sequence of either the target nucleic acid sequence or the non-target nucleic acid sequence, under conditions to incorporate the first labelled nucleotide either into the primer hybridised to the target nucleic acid sequence or into the primer hybridised to the non-target nucleic acid sequence but not into both;

(c) subjecting the preparation to a sequencing reaction, thereby extending the primer to form one or more first-labelled sequencing products comprising the first labelled nucleotide and one or more non-first-labelled sequencing products comprising no first labelled nucleotide; and (d) determining at least a portion of the sequence of the first-labelled sequencing products and/or the non-first-labelled sequencing products, thereby determining at least the second region of dissimilar sequence of the target nucleic acid sequence.

The present invention provides an improved method of sequencing a target nucleic acid sequence comprised in a preparation comprising a different but related nucleic acid sequence. The method advantageously allows the sequencing products derived from the target nucleic acid sequence to be distinguished from the sequencing products derived from the non-target nucleic acid sequence. The target-derived sequencing products can therefore be analysed separately from the sequencing products derived from the non-target nucleic acid sequence, and the target nucleic acid sequence can be determined.

The method is a fast and efficient way of discriminating between two related sequences. In particular, the method is advantageous because a sequence-specific sequencing primer does not have to be constructed for each target nucleic acid sequence. The method also does not suffer from problems relating to lack of discrimination in primer hybridisation to closely-related sequences.

The invention also provides a method for determining a target nucleic acid sequence and a second nucleic acid sequence. This method advantageously allows two related nucleic acid sequences to be determined using a single sequencing primer and a single sequencing reaction.

The method also provides an enhanced method for haplotyping. The method enables the rapid determination of allele associations to identify individually the two haplotype sequences present at a particular locus in a subject. The method is particularly advantageous in identifying associations of SNPs and in HLA genotyping. In particular, the method avoids the need for time-consuming family studies or prior knowledge of allele associations.

The target nucleic acid sequence of the present invention is not particularly limited. Suitable target nucleic acid sequences include a deoxyribonucleic acid (DNA) sequence, a ribonucleic acid (RNA) sequence, or a DNA or RNA sequence comprising one or more modified nucleotides or bases, or one or more artificial nucleotides or bases. The second nucleic acid sequence is likewise not particularly limited, and may be a DNA or RNA sequence, optionally comprising one or more modified nucleotides or bases.

Preferably the target nucleic acid sequence and/or the non-target nucleic acid sequence is a DNA sequence. The DNA sequence may be a genomic DNA or cDNA sequence. Each sequence is preferably a human DNA sequence. In a preferred embodiment, the target nucleic acid sequence and/or the non-target nucleic acid sequence is a PCR product.

The target nucleic acid sequence may be comprised in the same nucleic acid polymer as the non-target nucleic acid. However, the two nucleic acid sequences are preferably on separate DNA molecules. More preferably the target nucleic acid sequence and the non-target nucleic acid sequence each comprise one allele at a polymorphic genetic locus in a subject. In this embodiment, the target nucleic acid sequence comprises the locus on one chromosome of a pair (maternal or paternal) and the non-target nucleic acid sequence comprises the locus on the other chromosome of the pair.

In the present invention the preparation comprises a target nucleic acid sequence and a non-target nucleic acid sequence. Suitable preparations include any preparation comprising two or more nucleic acid sequences, provided that at least two of the nucleic acid sequences share a region of common sequence but differ in a region of dissimilar sequence. Preferably the preparation comprises a purified DNA preparation. The preparation is preferably prepared from a sample derived from a single human subject. Thus the preparation may be a sample of human saliva, blood, urine or other tissue, or a DNA preparation comprising genomic DNA which has been prepared from such a sample.

Each of the two nucleic acid sequences includes a first region of common sequence. This means that the target nucleic acid sequence is identical to the non-target nucleic acid sequence in this region. The method advantageously allows discrimination of sequencing products derived from the target nucleic acid sequence from those derived from the non-target nucleic acid sequence, despite the fact that a generic primer which is complementary to the region of common sequence (and therefore hybridises to both nucleic acid sequences) is used.

The first region of common sequence preferably comprises a length of at least 10 nucleotides, more preferably at least 20 nucleotides.

The first region of common sequence is upstream of a first region of dissimilar sequence. The first region of dissimilar sequence is upstream of a second region of dissimilar sequence. By "upstream" it is meant upstream in terms of the direction of sequencing. The sequencing primer first hybridises to a region comprising at least a portion of the first region of common sequence. As the primer is extended (in the downstream direction) the first region of dissimilar sequence acts as a template for primer extension before the second region of dissimilar sequence. Because primer extension typically proceeds in the 5' to 3' direction (as nucleotides are added at the 3' end of the nascent chain), the first region of common sequence typically lies 3' to the first region of dissimilar sequence, and the first region of dissimilar sequence typically lies 3' to the second region of dissimilar sequence.

By "region of dissimilar sequence" it is meant that the sequence of the target nucleic acid is different from the non-target nucleic acid in this region. In one embodiment the first and second regions of dissimilar sequence are contiguous, that is the second region of dissimilar sequence immediately follows the first region of dissimilar sequence with no intervening region of common sequence. In an alternative embodiment, the first and second dissimilar sequences are separated by a second region of common sequence. This is illustrated in FIG. 6. FIG. 6 shows a target nucleic acid 1 and a non-target nucleic acid 2. The target nucleic acid and non-target nucleic acid each have a first region of common sequence 3, a first region of dissimilar sequence 4 and a second region of dissimilar sequence 6. In the embodiment shown, a second region of common sequence 5 lies between the first and second regions of dissimilar sequence. Third and fourth regions of dissimilar sequence (8 and 10) and third, fourth and fifth regions of common sequence (7, 9 and 11) are also shown.

In one embodiment the target nucleic acid sequence and the non-target nucleic acid sequence comprises one or more further regions of dissimilar sequence. For instance, there may be a third, fourth, fifth or subsequent regions of dissimilar sequence downstream of the second region of dissimilar sequence. However, there must be at least two regions of dissimilar sequence. Each region of dissimilar sequence is separated by a further region of common sequence. The method permits the determination of the sequence of the target nucleic acid sequence downstream of the second region of dissimilar sequence as far as the sequencing reaction is capable of proceeding.

The length of the first and second regions of dissimilar sequence is not particularly limited. Any length of dissimilar sequence may be used from a single nucleotide upwards. In a preferred embodiment, either or both regions of dissimilar sequence comprises an SNP.

The method comprises a step of contacting a preparation with an oligonucleotide primer complementary to at least a portion of the first region of common sequence. This means that at least a portion of the primer is complementary to a sequence which is present in both the target nucleic acid sequence and the non-target nucleic acid sequence. Thus the primer is capable under suitable conditions (and in the absence of any blocking agent) of hybridising to both the target nucleic acid sequence and the non-target nucleic acid sequence.

In a preferred embodiment, the primer is complementary to a sequence which is found entirely within the first region of common sequence. This means that the hybridisation site of the primer has an identical sequence in both the target and non-target nucleic acid sequence. However, in an alternative embodiment a primer may be used which is capable of hybridising to a sequence a part of which differs between the target nucleic acid sequence and the non-target nucleic acid sequence. In this embodiment, the primer may be fully complementary to a sequence found in either the target or non-target nucleic acid sequence, but a part of the primer may not be complementary to the other nucleic acid sequence. Thus, only a part of the primer is capable of hybridising to one of the nucleic acid sequences. Alternatively, a mixed primer may be used such that the primer contains two species, a first species complementary to the target nucleic acid sequence and a second species complementary to the non-target nucleic acid sequence. The difference in sequence between the target and non-target nucleic acid sequence in the region to which the primer hybridises preferably should be limited to one or two nucleotides, more preferably one nucleotide. The differences should also be located in a region of the nucleic sequences towards which the 5' end of the primer hybridises. If mismatches are located near the 3' end of the primer, it is more likely that polymerisation will be inhibited. These embodiments fall within the scope of the invention provided that under the hybridisation conditions employed, the primer is not capable of selectively hybridising only to one of the two nucleic acid sequences.

The nature of the primer is not particularly limited, provided that it is capable of initiating a sequencing reaction when hybridised to a nucleic acid. Preferably the primer is a single-stranded DNA. The length of the primer is preferably 5 to 50 nucleotides, more preferably 10 to 50 nucleotides, more preferably 10 to 40 nucleotides and most preferably 15 to 30 nucleotides. Suitable primers may be designed according to standard techniques known to those skilled in the art for selecting primers for polymerase reactions, such as for sequencing and for amplification of DNA by the polymerase chain reaction (PCR).

The preparation is contacted with the primer, typically by adding an aqueous solution of the primer to a preparation containing a suitable amount of nucleic acid. Hybridisation conditions are then selected so that the primer hybridises to the first region of common-sequence of the nucleic acid, according to criteria well known to those skilled in the art. An appropriate temperature and salt content for hybridisation needs to be selected according to the length of the oligonucleotide primer and its G-C content, amongst other things (Old & Primrose (1994), *Principles of Gene Manipulation*, Blackwell Science and Maniatis et al. (1992), *Molecular Cloning, A Laboratory Manual*, Cold Spring Harbor Laboratory, New York. Typically the hybridisation temperature should be close to the melting temperature ($T_m$) of the primer. $T_m$ is defined as the temperature at which the primer and its target are 50% dissociated, and for oligonucleotide primers may be calculated according to the "Wallace rule" by the following formula:

$$T_m = 4 \times (\text{number of } G{:}C \text{ base-pairs}) + 2 \times (\text{number of } A{:}T \text{ base-pairs})$$

Preferably the hybridisation temperature should be within 2° C. of $T_m$. Accordingly, for a 20-mer oligonucleotide probe with 50% G-C content, the $T_m$ is about 60° C. and a suitable hybridisation temperature would be 58° C.

The present method includes a step of contacting the preparation with a first labelled nucleotide. This labelling step is typically performed before the sequencing reaction is initiated, but may alternatively be performed after the sequencing reaction has been initiated, provided that substantially no primer has been extended into the second region of dissimilar sequence of the non-target nucleic acid.

The labelling step results in the incorporation of the first labelled nucleotide into either the primer hybridised to the target nucleic acid sequence or into the primer hybridised to the non-target nucleic acid sequence. The primer may be unextended at this stage or may be partially extended provided that it has not been extended as far as the second region of dissimilar sequence. The labelling step enables the sequencing products derived from the target nucleic acid sequence to be distinguished from the sequencing products derived from the non-target nucleic acid sequence. The method also allows a particular sequence in the first region of dissimilar sequence to be determined as being associated with a particular sequence in the second region of dissimilar sequence, by only introducing a first labelled nucleotide into a nucleic acid sequence when a particular nucleotide is present at the first region of dissimilar sequence.

It is not particularly important whether the first labelled nucleotide is incorporated into the primer hybridised to the target nucleic acid sequence or into the primer hybridised to the second nucleic acid sequence, provided that it is not incorporated into both. In one embodiment, the first labelled nucleotide is incorporated into the primer hybridised to the target nucleic acid sequence, so that the first labelled sequencing products are derived from the target nucleic acid sequence. In another embodiment, the first labelled nucleotide is incorporated into the primer hybridised to the non-target nucleic acid sequence, so that the first labelled sequencing products are derived from the non-target nucleic acid sequence.

The first labelled nucleotide may comprise any type of label, provided that the label enables the first-labelled sequencing products to be distinguished from the non-first-labelled sequencing products. Suitable labels include fluorescent labels, such as fluorescein, Rhodamin, Texas Red, CY-5 and CY-3. Alternatively the label may comprise one part of a ligand-affinant pair. A preferred ligand-affinant pair is biotin-streptavidin. In this embodiment, the label preferably comprises biotin. The ligand-affinant pair may also be antigen-antibody. In this embodiment the antigen may comprise hapten, for example dinitrophenyl.

It is important to ensure that the first labelled nucleotide is incorporated only into the primer hybridised to the target nucleic acid sequence, or is incorporated only into the primer hybridised to the non-target nucleic acid sequence. The amount of first labelled nucleotide incorporated into one of the two nucleic acid sequences should be low to undetectable, and preferably substantially no first-labelled nucleotide should be incorporated into the primer hybridised to one of the two nucleic acid sequences.

One way to ensure that the first labelled nucleotide is incorporated only into one of the two nucleic acid sequences is to employ a first labelled nucleotide which is complementary to a first template nucleotide at a particular position in one of the two nucleic acid sequences, but is not complementary to a second template nucleotide at a corresponding position in the other of the two nucleic acid sequences. In a preferred embodiment, the first labelled nucleotide is complementary to a first template nucleotide comprised in the first region of dissimilar sequence of either the target nucleic acid sequence or the non-target nucleic acid sequence. For instance, where the first labelled nucleotide is complementary to a first template nucleotide comprised in the first region of dissimilar sequence of the target nucleic acid sequence, the first labelled nucleotide will not be complementary to a second template nucleotide at a corresponding position in the non-target nucleic acid sequence.

The conditions employed to incorporate the first labelled nucleotide into the primer are not particularly limited. Typically a nucleic acid polymerase, such as a DNA polymerase is used to catalyse the addition of the first labelled nucleotide to the 3' terminus of the primer.

The preparation is then subjected to a sequencing reaction. The sequencing reaction may be any type of nucleic acid sequencing reaction, provided that it involves extension or elongation of the primer when hybridised to a nucleic acid sequence. Primer extension is typically performed using a DNA polymerase, such as *Thermus aquaticus* or Pfu DNA polymerase for reactions involving a high-temperature step, or other suitable DNA polymerases such as Klenow DNA polymerase where there is no high-temperature step. Preferably the sequencing reaction comprises Sanger sequencing using dideoxynucleotides. In another embodiment, the sequencing reaction comprises real-time sequencing, such as pyrosequencing.

The sequencing reaction proceeds into the second region of dissimilar sequence of the target nucleic acid sequence. Typically this means that at least some of the primer hybridised to the target nucleic acid sequence is extended so that the extended primer contains incorporated nucleotides complementary to one or more nucleotides in the second region of dissimilar sequence of the target nucleic acid. In certain embodiments involving the use of dideoxynucleotide terminator sequencing, only a fraction of the primer may be extended into the second region of dissimilar sequence, as some of the extending primer is terminated at each position in order to determine the sequence.

In a preferred embodiment, a primer is used which is complementary to a region of common sequence, wherein the 3' nucleotide of the primer is complementary to a nucleotide in each nucleic acid which is immediately 5' to the first nucleotide of the first region of dissimilar sequence. Thus when the primer hybridises to each nucleic acid, it is immediately adjacent to the first region of dissimilar sequence. A first labelled nucleotide is then added which is complementary to a first template nucleotide at that position in the target nucleic acid sequence, but not to a second template nucleotide at the corresponding position in the non-target nucleic acid sequence. Unincorporated first labelled nucleotide is then removed, either by washing (especially if the nucleic acid is linked to a solid support) or by the use of a nucleotide-degrading enzyme, such as apyrase. The preparation is then subjected to a sequencing reaction, without allowing the primer to separate from the nucleic acid to which it is bound. In this way, the sequencing reaction produces first labelled sequencing products derived from the target nucleic acid sequence and non-first-labelled sequencing products derived from the non-target nucleic acid sequence.

It will be apparent that in an alternative embodiment to that described in the above paragraph, a first labelled nucleotide could be used which is complementary to a first template nucleotide at a particular position in the non-target nucleic acid sequence, in order to produce first labelled sequencing products derived from the non-target nucleic acid sequence and non-first-labelled sequencing products derived from the target nucleic acid sequence.

BRIEF DESCRIPTION OF THE DRAWING

In FIG. 1 a primer is shown as hybridised to a sequence immediately upstream of a single nucleotide polymorphism, which consists of an deoxyadeonsine nucleotide in allele A and a deoxyguanosine in allele G. As shown in FIG. 2, deoxycytidine triphosphate bearing a first label is then added and becomes incorporated into the primer hybridised to allele G. Unincorporated labelled deoxycytidine triphosphate is then removed and a sequencing reaction is performed in order to produce first-labelled sequencing products derived from allele G and non-first-labelled sequencing products derived from allele A.

DETAILED DESCRIPTION OF PREFERRED EMBODIMENTS

Figure 1:
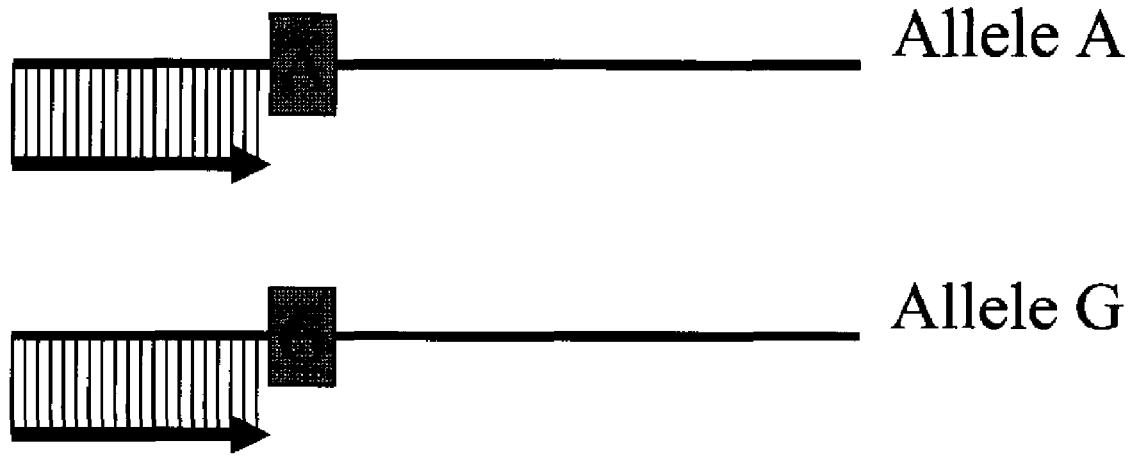
FIGS. 1 to 4 illustrate one embodiment of a method as described in the preceding two paragraphs.

The sequencing reaction is typically performed using a single primer extension step. It is important to ensure that the primer does not separate from the target and non-target nucleic acid sequences during the sequencing reaction, as this would allow non-first-labelled sequencing products to be produced using both nucleic acid sequences as templates. Accordingly, it is preferable to maintain the temperature of the sequencing reaction below the denaturation temperature of the primer/nucleic acid complex. For double-stranded nucleic acid templates, such as double-stranded DNA, the preparation can first be heated to an elevated temperature, such as 95° C. in order to separate the DNA strands. The preparation is then typically cooled to a suitable hybridisation temperature for the primer (such as 60° C. for a 20-mer oligonucleotide with 50% G-C content). Following addition of the terminator nucleotide and the removal of unincorporated terminator, the sequencing reaction is then performed at a constant temperature (such as 60 to 72° C. for a thermostable polymerase or 20 to 37° C. for a non-thermostable polymerase) without thermocycling.

If more than one primer extension step is required (for instance if the amount of starting template nucleic acid is too low to allow adequate detection of the sequencing products obtained by a single primer extension step), the method can be adapted as follows. After a first round of the sequencing reaction has been performed, the sequencing products are denatured from the target and non-target nucleic acid sequences by raising the temperature. The temperature is then lowered to allow any remaining primer in the preparation to hybridise to the target and non-target nucleic acid sequences. If necessary, further primer may be added at this stage. Steps (b) and (c) are then repeated. By adding further first labelled nucleotide and thereby producing further sequencing products as steps (b) and (c) are repeated, the determination of the sequence of the sequencing products in step (d) is facilitated).

Where a sequencing method based on dideoxynucleotide terminators is employed, four separate sequencing reactions may be performed, each containing one dideoxy terminator (dATP, dCTP, dGTP or dTTP) and the products visualised in separate lanes by polyacrylamide gel electrophoresis and autoradiography. Alternatively, if dye terminators comprising fluorescent labels are employed, wherein the labels fluoresce at different wavelengths to indicate each particular terminator nucleotide, a single sequencing reaction can be used.

In an alternative embodiment, the sequencing reaction comprises a method of sequencing based on the detection of the release of pyrophosphate. Applicable methods are disclosed in WO 98/28440 and in Science (1998) Vol 281, pages 363 to 365, the contents of which are incorporated herein by reference. Such methods have been termed "pyrosequencing". According to one suitable pyrosequencing method, the nucleic acid to be sequenced is incubated with the primer, DNA polymerase, ATP sulfurylase, firefly luciferase and a nucleotide-degrading enzyme such as apyrase. Four nucleotides are added stepwise, wherein a nucleotide will only become incorporated into the growing DNA strand and release pyrophosphate (PPi) if it is complementary to the base in the template strand. Any release of PPi is detected enzymically, for example by an enzyme cascade resulting in the production of light which is detected in a suitable light-sensitive device such as a luminometer or a charge-coupled device camera. Unincorporated nucleotides are degraded between each cycle by the nucleotide-degrading enzyme, so that after the first nucleotide has been degraded, the next nucleotide can be added. As this procedure is repeated, longer stretches of the template sequence are deduced.

Pyrosequencing is preferably performed using a single-stranded template, which may be suitably prepared by biotin capture of one strand on magnetic beads. The single-stranded template may be free in solution or immobilised on a solid support. Alternatively, a double-stranded DNA template may be employed if the enzymes used in the method are thermostable. In such an embodiment a single heating step is used to denature the double-stranded DNA, followed by a step in which the primer is allowed to anneal. Following the labelling step the extending primer is not separated from its template.

Earlier methods based on the detection of the release of pyrophosphate such as those disclosed in WO 93/23562 and WO 98/13523 are also applicable in the present invention. These methods do not use a nucleotide-degrading enzyme, and therefore require immobilisation of DNA on a solid support and washing steps between each nucleotide addition.

When a method involving the stepwise addition of individual nucleotides (such as pyrosequencing) is used, the primer need not necessarily hybridise immediately adjacent to the first region of dissimilar sequence. Nucleotides can be added stepwise until the first region of dissimilar sequence is reached. At this point, a labelled nucleotide can be added which is complementary to a nucleotide at this position in, for instance, the target nucleic acid sequence. The labelled nucleotide is not complementary to a nucleotide at the corresponding position in the non-target nucleic acid sequence. The "corresponding position" is determined relative to the primer binding site or the start of the first region of dissimilar sequence. Because the primer hybridises to an identical sequence in both the target and non-target nucleic acid sequences, a corresponding position in the target nucleic acid sequence may be defined as being a particular number of nucleotides downstream of the last nucleotide of the primer binding site, or a particular number of nucleotides downstream of the first nucleotide of the first region of dissimilar sequence. The labelled nucleotide will then become incorporated only into the target nucleic acid sequence.

In step (d) of the present method, at least a portion of the sequence of either the first-labelled or the non-first-labelled sequencing products is determined. In an embodiment where in step (b) the first labelled nucleotide is incorporated into the primer hybridised to the target nucleic acid sequence, in step (d) at least a portion of the sequence of the first-labelled sequencing products is determined. In an alternative embodiment where in step (b) the first labelled nucleotide is incorporated into the primer hybridised to the non-target nucleic acid sequence, in step (d) at least a portion of the sequence of the non-first-labelled sequencing products is determined. In one embodiment, at least a portion of the sequence of both the first-labelled and non-first-labelled sequencing products is determined.

The method of determining the sequence of the sequencing products is not particularly limited, provided that it is capable of discriminating between the first-labelled and non-first-labelled sequencing products. In embodiments where the labelled nucleotide comprises a fluorescent label, the method of sequencing is preferably based on dideoxyterminators and the sequencing products are separated by gel electrophoresis. In this embodiment, preferably four separate sequencing reactions are performed, each containing one dideoxy terminator (dATP, dCTP, dGTP or dUTP). Either the primer or the terminator nucleotide may optionally comprise a further label, so that all sequencing products of a particular length can be visualised. The further label may be label which fluoresces at a different wavelength to the labelled nucleotide, or may be radiolabel. All sequencing products may be visualised by detecting the further label and their length determined by their rate of migration in the gel. The sequence of the first-labelled sequencing products may be determined by identifying those sequencing products which fluoresce at the appropriate wavelength. The sequence of the non-first-labelled sequencing products may be determined by identifying those sequencing products which do not fluoresce at the appropriate wavelength. Where the further label comprises a label which fluoresces at a different wavelength to the labelled nucleotide an automated sequencer capable of simultaneous detection of two or more fluorescent labels may be used.

In an alternative embodiment, the first-labelled sequencing products are physically separated from the non-first-labelled sequencing products before determining their sequence. This embodiment preferably comprises a separating step of contacting the first-labelled and non-first-labelled sequencing products with a solid phase under conditions to bind the first-labelled sequencing products but not the non-first-labelled sequencing products to the solid phase. Alternatively the separating step may be performed after step (b) and before step (c), in order to separate the first-labelled primer/nucleic acid sequence complex from the non-first-labelled primer/nucleic acid sequence complex before performing the sequencing reaction.

The solid phase preferably comprises magnetic beads, more preferably streptavidin-coated magnetic beads. Preferably the solid phase and first labelled nucleotide together comprise a ligand-affinant pair. More preferably the solid phase comprises streptavidin and the first-labelled nucleotide comprises a biotin label.

The solid phase with bound first-labelled sequencing products is then separated from the liquid phase comprising the non-first-labelled sequencing products preferably by washing. The first-labelled sequencing products may optionally be eluted from the solid phase before their sequence is determined.

In embodiments where the method of sequencing comprises a real-time method such as pyrosequencing, the sequencing reaction and sequence determination steps (steps (c) and (d)) are substantially simultaneous. In these embodiments, the separating step must be performed after step (b) and before step (c).

In a further embodiment the present invention, the method comprises a further step of contacting the preparation with a second labelled nucleotide which is distinguishable from the first labelled nucleotide. The second labelled nucleotide is incorporated into the non-first-labelled sequencing products, and serves to further aid discrimination between the sequencing products derived from the target and non-target nucleic acid sequences. For instance, in one embodiment the second labelled nucleotide comprises a ligand such that the first labelled and non-first-labelled sequencing products can be bound to separate solid phases, which assists in their separation. Alternatively the first and second labelled nucleotides may comprise different fluorescent labels such that sequencing products comprising each label may be discriminated more effectively during or after gel electrophoresis.

Figure 2:
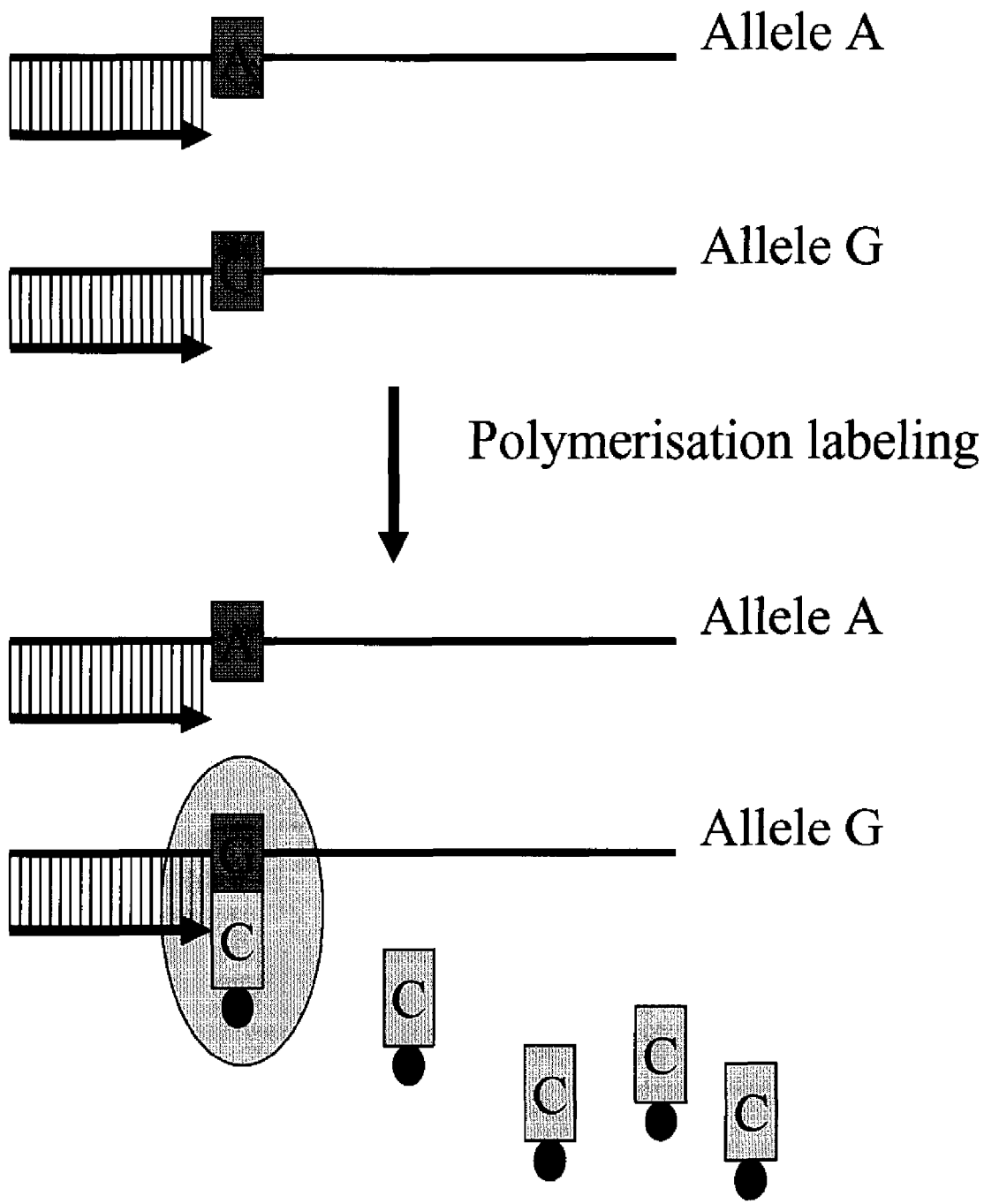
Figure 3:
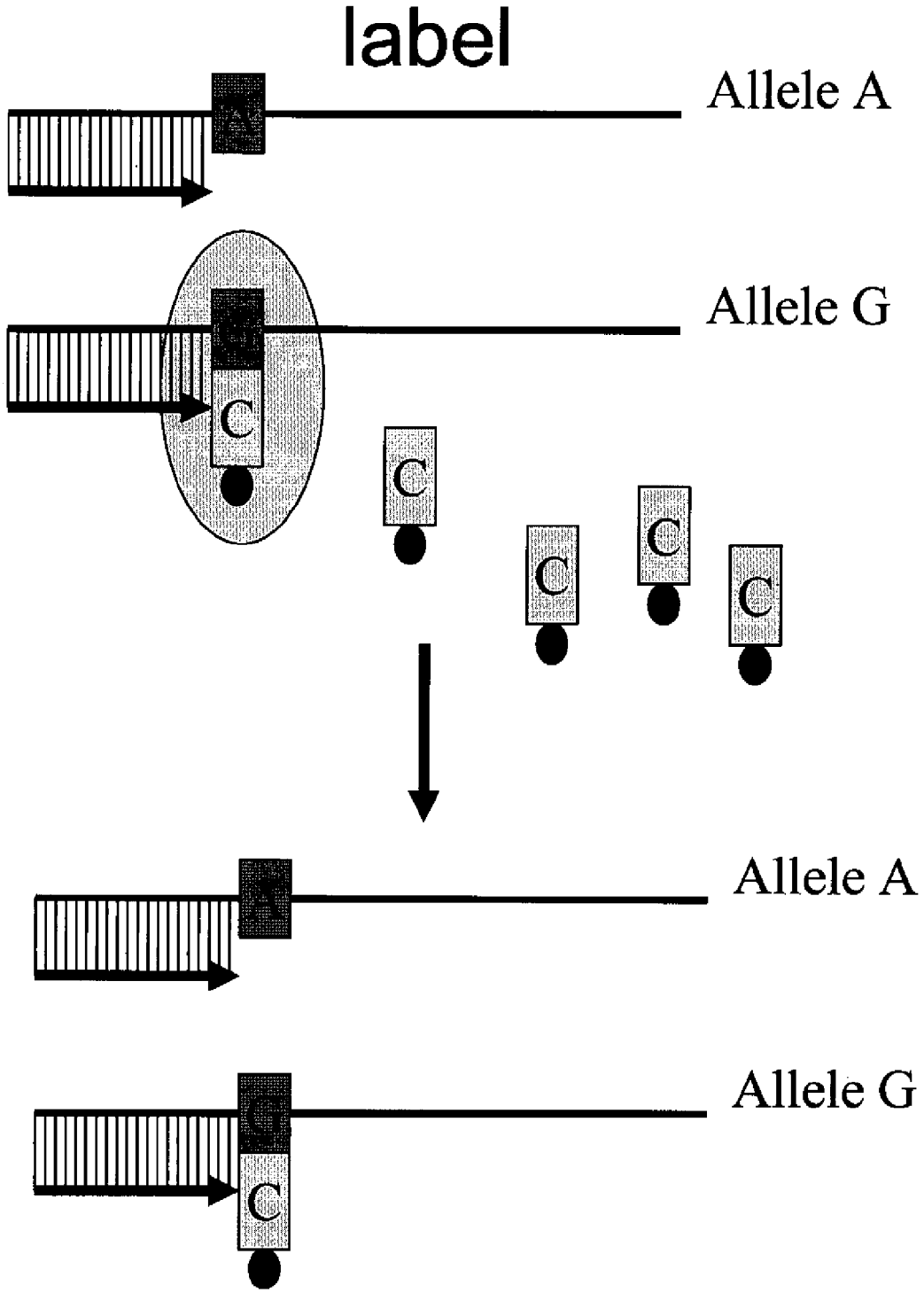
Figure 4:
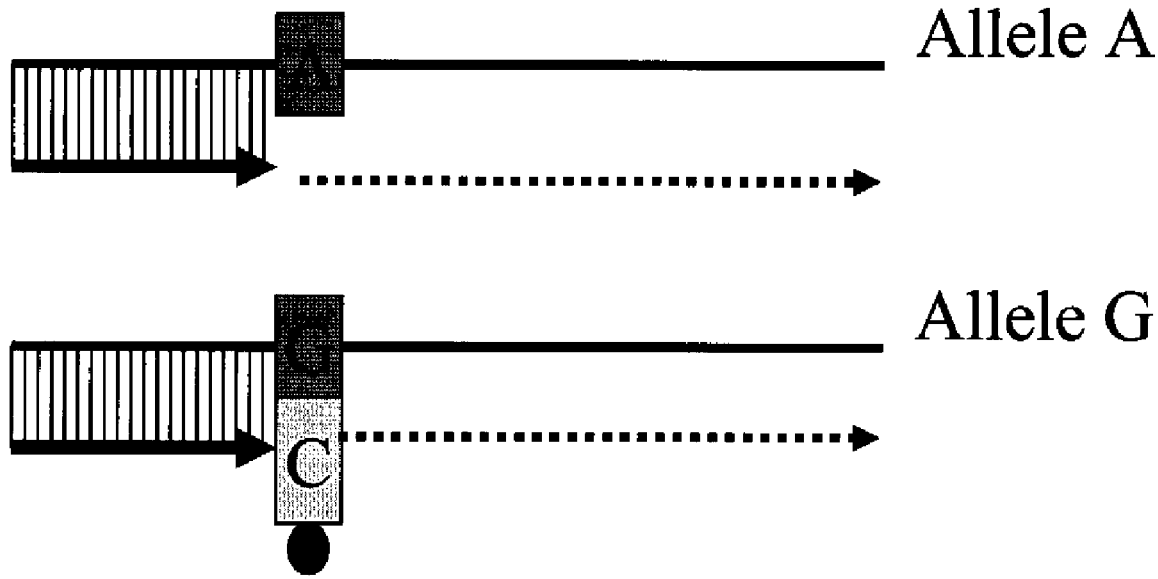
Figure 5:
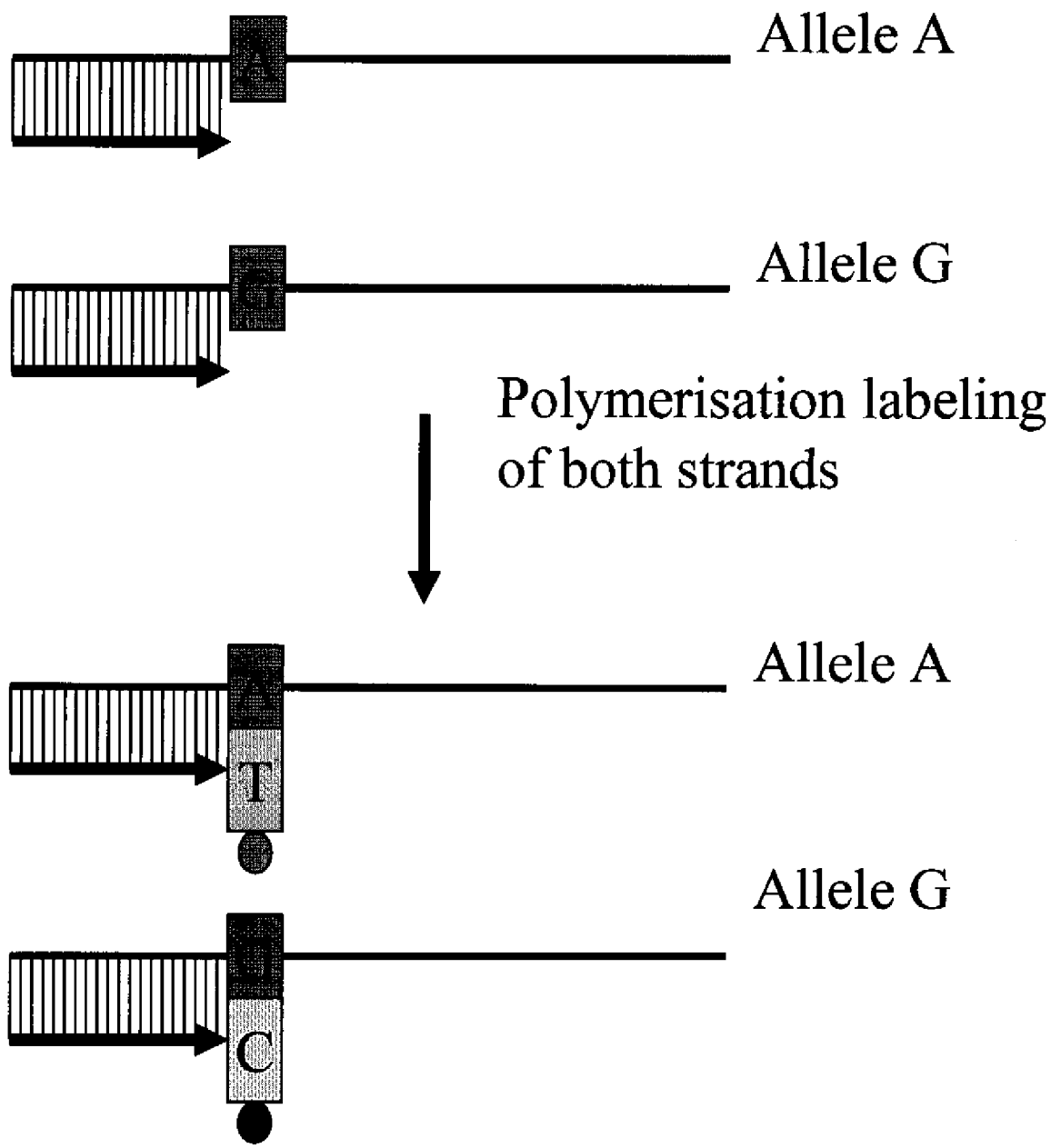
Figure 6:
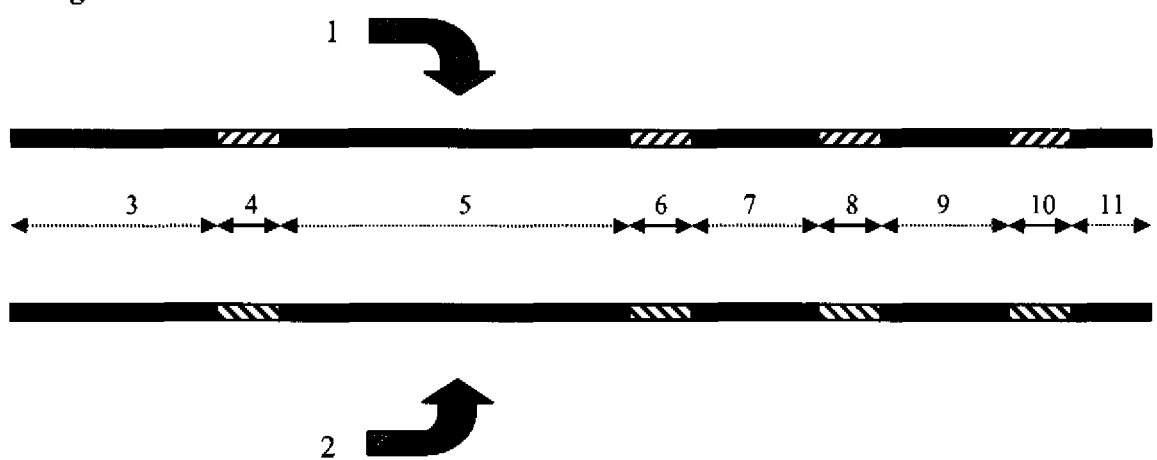

FIG. 5 illustrates a modification of the step shown in FIG. 2 of the method shown in FIGS. 1 to 4, comprising the further step of contacting the preparation with a second labelled nucleotide. In this embodiment, the preparation is contacted with deoxythymidine triphosphate bearing a second label in addition to deoxycytidine triphosphate bearing a first label, wherein the second label is distinguishable from the first label. One or more first-labelled sequencing products derived from allele G are produced which bear the first label, and one or more non-first labelled sequencing products derived from allele A are producing which bear the second label.

According to the present invention, by labelling sequencing products derived from either a target or non-target nucleic acid sequence at least the second region of dissimilar sequence of the target nucleic sequence may be determined. If both the first-labelled and non-first-labelled sequencing products are analysed, both the target and non-target nucleic acid sequences may be determined.

In one aspect, the present invention provides a method for determining a target nucleic acid sequence and a non-target nucleic acid sequence (while this nucleic acid sequence is conveniently referred to as non-target; this method does enable the sequencing of this non-target sequence). Preferably this method includes a step of contacting the preparation with a second labelled nucleotide as described above, and includes a step of determining a portion of the sequence of the non-first-labelled sequencing products, so that at least the second region of dissimilar sequence of the non-target nucleic acid sequence is also determined. In a preferred embodiment, the first labelled nucleotide comprises a first fluorescent label and the second labelled nucleotide comprises a second fluorescent label, wherein the first and second fluorescent labels fluoresce at different wavelengths. The first labelled nucleotide is complementary to a first template nucleotide comprised in the first region of dissimilar sequence of the target nucleic acid sequence, and the second labelled nucleotide is complementary to a second template nucleotide comprised in the first region of dissimilar sequence of the non-target nucleic acid sequence. The first labelled nucleotide is incorporated into the primer hybridised to the target nucleic acid sequence and the second labelled nucleotide is incorporated into the primer hybridised to the non-target nucleic acid sequence. Four separate sequencing reactions are carried out, each containing one dideoxy terminator. The sequencing products from each reaction are visualised by gel electrophoresis in separate lanes. Each lane contains first-labelled sequencing products derived from the target nucleic acid sequence and non-first-labelled sequencing products derived from the non-target nucleic acid sequence. The first fluorescent label and the second fluorescent label are detected, preferably by an automatic sequencer, so that the sequence of both the target and non-target nucleic acid sequences may be determined.

In one embodiment, the preparation comprises one or more further nucleic acid sequences, wherein each further nucleic acid sequence has a first region of common sequence upstream of a first region of dissimilar sequence upstream of a second region of dissimilar sequence. Here "common sequence" means that the sequence of the further nucleic acid sequence is identical to the target and non-target nucleic acid sequences in this region. "Dissimilar sequence" means that the sequence of the further nucleic acid is different from the target and/or non-target nucleic acid sequences in this region.

By using the methods described below, the sequence of particular further nucleic acid sequences may be determined. This type of analysis may be termed "multiplexing". Multiplexing permits the analysis of multiple sites in an individual sample or a number of samples from different individuals.

In one embodiment using multiplexing, the preparation comprises DNA derived from samples taken from two or more individuals. For instance, a number of DNA preparations derived from different individuals in a group may be combined and the method described herein carried on the combined preparation. This method may be used to assess whether or not a particular combination of SNPs is found together on a single chromosome in all individuals within the group. If so, the sequencing reaction will yield a single sequence. If not, the sequencing reaction will indicate alternative bases at the position of one or more SNPs in the sequence. If it is then desired to determine which combination of SNPs was present in which individual, it would be necessary to repeat the method on separate DNA preparations from each individual.

In another embodiment involving multiplexing, more than one target nucleic acid sequence may be determined using a single sequencing reaction. In this embodiment, the present method is performed in parallel using two or more oligonucleotide primers, each of which is complementary to a different sequence. In this way, two or more polymorphic sites may be analysed simultaneously. Each target nucleic acid sequence shares a first region of common sequence with a corresponding non-target nucleic acid sequence.

In one such embodiment, the invention relates to a method for determining a plurality of target nucleic acid sequences, wherein the plurality of target nucleic acid sequences is comprised in a preparation further comprising a plurality of corresponding non-target nucleic acid sequences, each target nucleic acid sequence in the preparation corresponds to one or more corresponding non-target nucleic acid sequences in the preparation, each target nucleic acid sequence and each corresponding non-target nucleic acid sequence has a first region of common sequence upstream of a first region of dissimilar sequence upstream of a second region of dissimilar sequence, the first region of common sequence of each target nucleic acid sequence is the same as the first region of common sequence of its corresponding non-target nucleic acid sequences, the first region of dissimilar sequence of each target nucleic acid sequence is different to the first region of dissimilar sequence of its corresponding non-target nucleic acid sequences, the second region of dissimilar sequence of each target nucleic acid sequence is different to the second region of dissimilar sequence of its corresponding non-target nucleic acid sequences, which method comprises:

(a) contacting the preparation with a plurality of oligonucleotide primers, wherein each primer is complementary to at least a portion of the first region of common sequence of a target nucleic acid sequence and its corresponding non-target nucleic acid sequence, under conditions to hybridise the primer thereto; and (b) contacting the preparation with a plurality of first labelled nucleotides wherein each first labelled nucleotide bears a different first label, wherein each first labelled nucleotide is complementary to a first template nucleotide comprised in the first region of dissimilar sequence of a target nucleic acid under conditions to incorporate the first labelled nucleotide into the primer hybridised to the target nucleic acid sequence;

(c) subjecting the preparation to a sequencing reaction, thereby extending each primer to form one or more first-labelled sequencing products comprising a first labelled nucleotide and one or more non-first-labelled sequencing products comprising no first labelled nucleotide; and (d) determining at least a portion of the sequence of each different first-labelled sequencing product and/or each non-first-labelled sequencing product, thereby determining at least the second region of dissimilar sequence of each target nucleic acid sequence.

In this embodiment, sequencing reaction products are obtained which are derived from more than one target nucleic acid sequence. The sequencing reaction products derived from each target nucleic acid sequence are discriminated between by the distinct labelling of the sequencing reaction products derived from each target nucleic acid sequence. In one embodiment, each target nucleic acid sequence is labelled with a fluorescent label which fluoresces at a different wavelength. Sequencing products derived from each target nucleic acid sequence may then be distinguished for example using an automated sequencer following gel electrophoresis. In another embodiment, one or more target nucleic acid sequence is labelled with one part of a ligand-affinant pair. A preferred ligand-affinant pair is biotin-streptavidin. The ligand-affinant interaction may be used in order to bind sequencing products derived from one target nucleic acid sequence to a solid phase (such as magnetic beads), thereby separating the labelled sequencing products from non-labelled sequencing products. The labelled and non-labelled sequencing may then be separately subjected to gel electrophoresis.

In a preferred embodiment of the present invention, the method involves determining the combination of individual SNPs which exist in a particular region on one chromosome of a pair in a subject. Determining the association of alleles such as SNPs is termed haplotyping. In this embodiment, each of the first and second regions of dissimilar sequence comprise a single nucleotide. The target nucleic acid sequence comprises a particular locus (such as a particular gene, part of a gene or regulatory element) on one chromosome of a pair in the individual subject, and the non-target nucleic acid sequence comprises the corresponding sequence on the other chromosome in the pair. The locus comprises two or more SNPs. The first and second regions of common sequence comprise parts of the locus which are non-polymorphic between the two chromosomes.

Where the method is used to determine associations of previously identified SNPs in a subject sample, a labelled nucleotide complementary to one of the known alleles for the first SNP may be selected in order to label all sequencing products derived from primer hybridisation to one chromosome of a pair. In this way, the first labelled sequencing products will all be derived from one chromosome and the non-first-labelled sequencing products will all be derived from the other chromosome of the pair. By determining the sequence of either the first-labelled or non-first-labelled sequencing products, a particular nucleotide at a second SNP can be determined to be on the same chromosome as a particular nucleotide at the first SNP.

For example, two alleles A (on chromosome A) and C (on chromosome A') for SNP-1 and two alleles G and T for SNP-2 may be known to be present within a particular gene in a subject, but the combination of alleles on each chromosome (haplotype) is unknown. The possible haplotypes (for chromosome A and its pair chromosome A') for this individual are therefore either (1) A-G (on chromosome A) and C-T (on chromosome A'), or (2) A-T and C-G. In order to distinguish between these possibilities, labelled deoxythymidine triphosphate is added to the preparation so that it becomes incorporated into the primer hybridised to chromosome A which bears an A at SNP-1. Labelled sequencing products are then produced which are derived from chromosome A. The unlabelled sequencing products are derived from chromosome A'. If sequencing of the labelled sequencing products reveals a G at SNP-2, then (1) is correct. Sequencing of the unlabelled sequencing products would be expected to reveal a T at SNP-2.

HLA genotyping is one area where haplotyping is particularly useful. Genotyping of the two haplotypes of the HLA genes is crucial to the success of the transplantation of organs and bone marrow. In a preferred embodiment, the locus comprises a human Class I or Class II HLA gene.

What is claimed is:

1. A method for determining a target nucleic acid sequence, the method comprising the steps of:
    (a) contacting a preparation comprising a target nucleic acid sequence and a non-target nucleic acid sequence, the target nucleic acid sequence and the non-target nucleic acid sequence each having a first region of common sequence upstream of a first region of dissimilar sequence upstream of a second region of dissimilar sequence—with an oligonucleotide primer complementary to at least a portion of the first region of common sequence, under conditions to hybridize the primer thereto;
    (b) contacting the resulting preparation with a first labeled nucleotide bearing a first label, wherein the first labeled nucleotide is complementary to a first template nucleotide comprised in the first region of dissimilar sequence of either the target nucleic acid sequence or the non-target nucleic acid sequence, under conditions to incorporate the first labeled nucleotide either into the primer hybridized to the target nucleic acid sequence or into the primer hybridized to the non-target nucleic acid sequence but not into both;
    (c) subjecting the so treated preparation to a sequencing reaction, thereby extending the primer to form one or more first-labeled sequencing products comprising the first labeled nucleotide and one or more non-first-labeled sequencing products comprising no first labeled nucleotide; and
    (d) determining the target nucleic acid sequence by determining at least a portion of the sequence of the first-labeled sequencing products and/or the non-first-labeled sequencing products, thereby determining at least the second region of dissimilar sequence of the target nucleic acid sequence.

2. The method according to claim 1, wherein the target nucleic acid sequence and the non-target nucleic acid sequence each have a second region of common sequence which lies between the first and second regions of dissimilar sequence.

3. The method according to claim 1, wherein the method further comprises the step of separating the first-labelled sequencing products from the non-first-labeled sequencing products.

4. The method according to claim 3, wherein the separating step comprises contacting the first-labeled and non-first-labeled sequencing products with a solid phase capable of binding to the first label.

5. The method according to claim 4, wherein the solid phase comprises magnetic beads.

6. The method according to claim 4, wherein the solid phase and the first label together comprise a ligand-affinant pair.

7. The method according to claim 6, wherein the solid phase comprises streptavidin and the first label comprises biotin.

8. The method according to claim 1, wherein the first label is fluorescent.

9. The method according to claim 1, wherein the method comprises the further step of contacting the preparation of step (b) with a second labeled nucleotide bearing a second label before carrying out step (c), the second label being distinguishable from the first label, under conditions such that the non-first-labeled sequencing products but not the first-labeled sequencing products formed in step (c) include the second labeled nucleotide.

10. The method according to claim 9, wherein the second label is fluorescent.

11. The method according to claim 1, wherein the first labeled nucleotide is complementary to a first template nucleotide comprised in the first region of dissimilar sequence of the target nucleic acid sequence and the first labeled nucleotide is not complementary to a second template nucleotide at a corresponding position in the non-target nucleic acid sequence.

12. The method according to claim 11, wherein the second labeled nucleotide is complementary to the second template nucleotide.

13. A method for determining a target nucleic acid sequence and a second nucleic acid sequence as defined in claim 12, wherein step (d) comprises determining at least a portion of the sequence of the first-labeled sequencing products and the non-first-labeled sequencing products, thereby determining at least the second region of dissimilar sequence of each of the target nucleic acid sequence and the non-target nucleic acid sequence.

14. The method according to claim 1, wherein the first region of dissimilar sequence comprises a single nucleotide.

15. The method according to claim 1, wherein the second region of dissimilar sequence comprises a single nucleotide.

16. The method according to claim 1, wherein the sequencing reaction comprises a method of sequencing based on the use of dideoxynucleotide terminators.

17. The method according to claim 1, wherein the preparation comprises DNA derived from two or more subjects.

18. A method for determining the haplotype of a subject from a sample comprising DNA from the subject according to the method as defined in claim 1, wherein the preparation comprises the sample, the target nucleic acid sequence comprises a locus on a first chromosome of a pair of chromosomes, the non-target nucleic acid sequence comprises the corresponding locus on the second chromosome of the pair, the locus comprising two or more single nucleotide polymorphisms for which the subject is heterozygous, wherein the sequencing reaction is conducted to determine the sequence of the locus on the first and/or the second chromosome of the pair, thereby determining the haplotype of the subject.

19. The method according to claim 18, wherein the target nucleic acid sequence and the non-target nucleic acid sequence comprise one or more further regions of dissimilar sequence downstream of the second region of dissimilar sequence.

20. The method according to claim 18, wherein the locus comprises a human Class I or Class II HLA gene.

21. A method for determining a plurality of target nucleic acid sequences, which method comprises the steps of:
(a) contacting a preparation wherein the plurality of target nucleic acid sequences is comprised in the preparation which further comprises a plurality of corresponding non-target nucleic acid sequences, each target nucleic acid sequence in the preparation corresponds to one or more corresponding non-target nucleic acid sequences in the preparation, each target nucleic acid sequence and each corresponding non-target nucleic acid sequence has a first region of common sequence upstream of a first region of dissimilar sequence upstream of a second region of dissimilar sequence, the first region of common sequence of each target nucleic acid sequence is the same as the first region of common sequence of its corresponding non-target nucleic acid sequences, the first region of dissimilar sequence of each target nucleic acid sequence is different to the first region of dissimilar sequence of its corresponding non-target nucleic acid sequences, the second region of dissimilar sequence of each target nucleic acid sequence is different to the second region of dissimilar sequence of its corresponding-non-target nucleic acid sequences, —with a plurality of oligonucleotide primers, wherein each primer is complementary to at least a portion of the first region of common sequence of a target nucleic acid sequence and its corresponding non-target nucleic acid sequence, under conditions to hybridize the primer thereto; and
(b) contacting the resulting preparation with a plurality of first labeled nucleotides wherein each first labeled nucleotide bears a different first label, wherein each first labeled nucleotide is complementary to a first template nucleotide comprised in the first region of dissimilar sequence of a target nucleic acid under conditions to incorporate the first labeled nucleotide into the primer hybridized to the target nucleic acid sequence;
(c) subjecting the so treated preparation to a sequencing reaction, thereby extending each primer to form one or more first-labeled sequencing products comprising a first labeled nucleotide and one or more non-first-labeled sequencing products comprising no first labeled nucleotide; and
(d) determining at least a portion of the sequence of each different first-labeled sequencing product, thereby determining at least the second region of dissimilar sequence of each target nucleic acid sequences.

22. A method of determining the haplotype of a subject comprising the steps of:
providing a sample comprising DNA from the subject to sequence a target locus on a first chromosome of a chromosome pair and a non-target locus on the second chromosome of the chromosome pair, wherein the target locus and the non-target locus each comprise two or more single nucleotide polymorphisms, and wherein the subject is heterozygous at each single nucleotide polymorphism; providing a primer that hybridizes to the target locus and the non-target locus upstream of the first single nucleotide polymorphism;
providing a first labeled nucleotide that is complementary to the nucleotide of the first single nucleotide polymorphism in either the target locus or the non-target locus wherein the label is a member of a ligand affinant pair;
contacting the sample, the primer and the first labeled nucleotide under conditions to hybridize the primer to the target locus and the non-target locus and to incorporate the first labeled nucleotide into the primer hybridized to either the target locus or the non-target locus, but not both;
separating the target locus/primer complex from the non-target locus/primer complex using the incorporated first labeled nucleotide;
extending the primer of the target/locus primer complex and/or the non-target locus primer complex in a pyrophosphate sequencing reaction to thereby determining a haplotype of the subject.

* * * * *